(12) United States Patent
Lanin et al.

(10) Patent No.: US 9,427,530 B2
(45) Date of Patent: Aug. 30, 2016

(54) DRUG DELIVERY DEVICE WITH RETRACTABLE NEEDLE

(75) Inventors: Irina Lanin, Frankfurt am Main (DE); Bernhard Forys, Frankfurt am Main (DE); Alastair Clarke, Cheshire (GB); Matthew Ekman, Cheshire (GB); Kirsten Goode, Frankfurt am Main (DE); Michael Heald, Cheshire (GB); John Hiles, Cheshire (GB); Chris Smith, Cheshire (GB); Lilly Hains-Gadd, Oxfordshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1394 days.

(21) Appl. No.: 13/201,452

(22) PCT Filed: Mar. 4, 2010

(86) PCT No.: PCT/EP2010/052786
§ 371 (c)(1),
(2), (4) Date: Jan. 25, 2012

(87) PCT Pub. No.: WO2010/100241
PCT Pub. Date: Sep. 10, 2010

(65) Prior Publication Data
US 2012/0136318 A1  May 31, 2012

(30) Foreign Application Priority Data
Mar. 5, 2009  (EP) .................................. 09003180

(51) Int. Cl.
*A61M 5/32* (2006.01)

(52) U.S. Cl.
CPC ............. *A61M 5/3234* (2013.01); *A61M 5/329* (2013.01); *A61M 2005/3223* (2013.01); *A61M 2005/3231* (2013.01)

(58) Field of Classification Search
CPC ............. A61M 2005/3223; A61M 2005/3231; A61M 5/158; A61M 5/3234; A61M 5/329; A61M 5/3293; A61M 5/343–5/346; A61M 5/348; A61M 5/322
See application file for complete search history.

(56) References Cited

U.S. PATENT DOCUMENTS

| 4,838,870 A | 6/1989 | Haber et al. |
| 4,995,870 A * | 2/1991 | Baskas ................... A61C 19/00 604/110 |
| 2004/0215150 A1 | 10/2004 | Shue et al. |

FOREIGN PATENT DOCUMENTS

| EP | 1547634 A1 * | 6/2005 | ............. A61M 5/32 |
| TW | EP 1547634 A1 * | 6/2005 | .......... A61M 5/3234 |

OTHER PUBLICATIONS

Form PCT/IB/326, Notification Concerning Transmittal of Copy of International Preliminary Report on Patentability. Mailed Sep. 15, 2011.

* cited by examiner

Primary Examiner — Bhisma Mehta
Assistant Examiner — Larry R Wilson
(74) Attorney, Agent, or Firm — McDonnell Boehnen Hulbert & Berghoff LLP

(57) ABSTRACT

Drug delivery device, comprising a needle, which a distal end and a proximal end comprises an inner surface forming a channel, an outer surface, a first salient located on the outer surface.

12 Claims, 7 Drawing Sheets

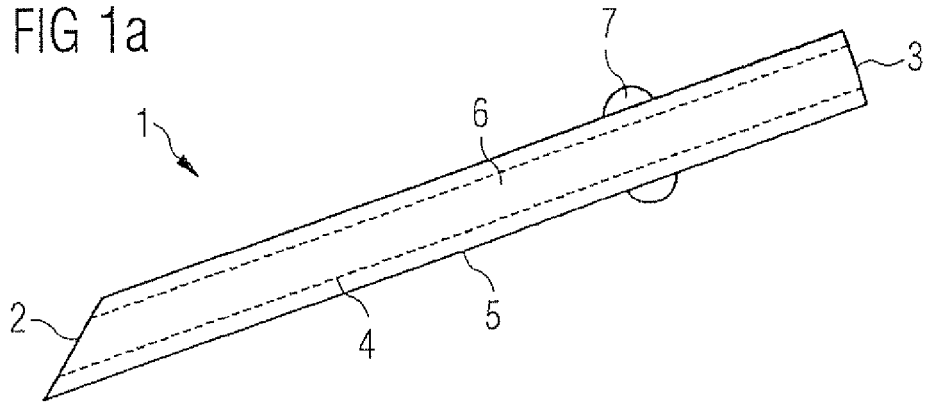
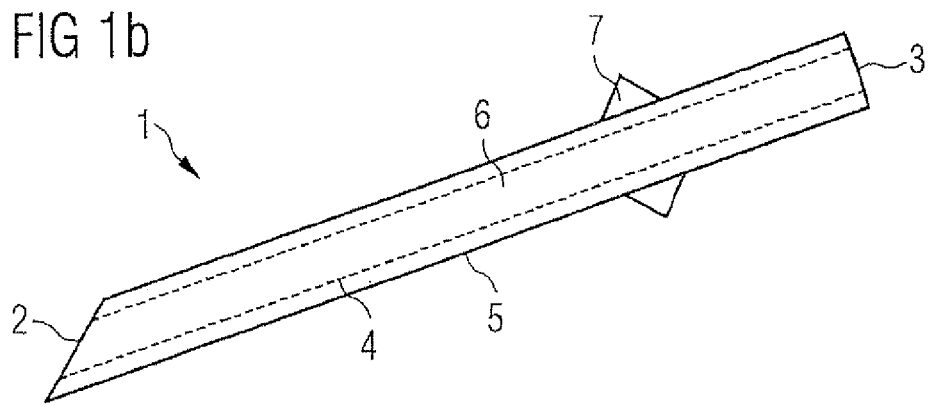
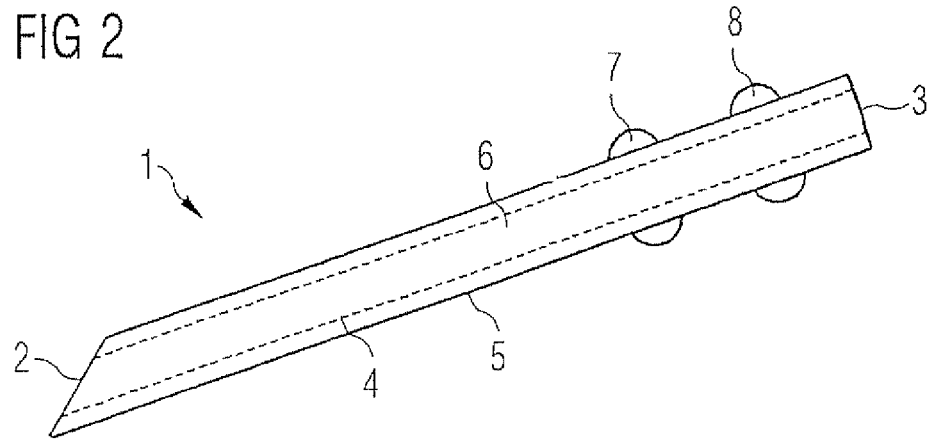

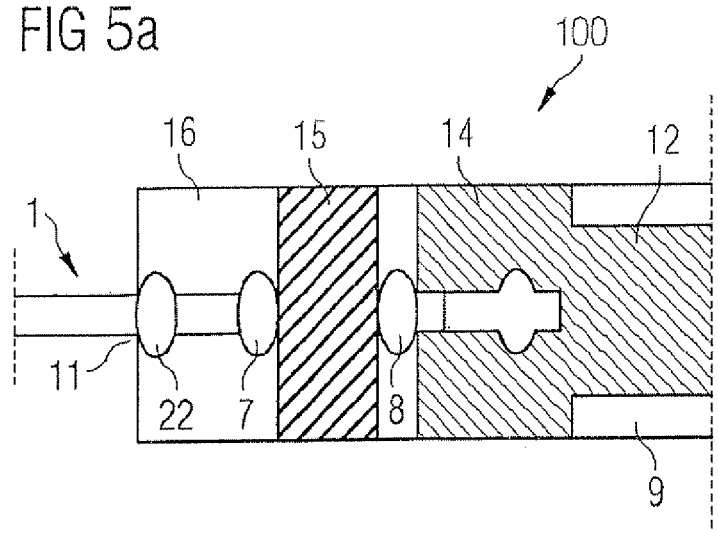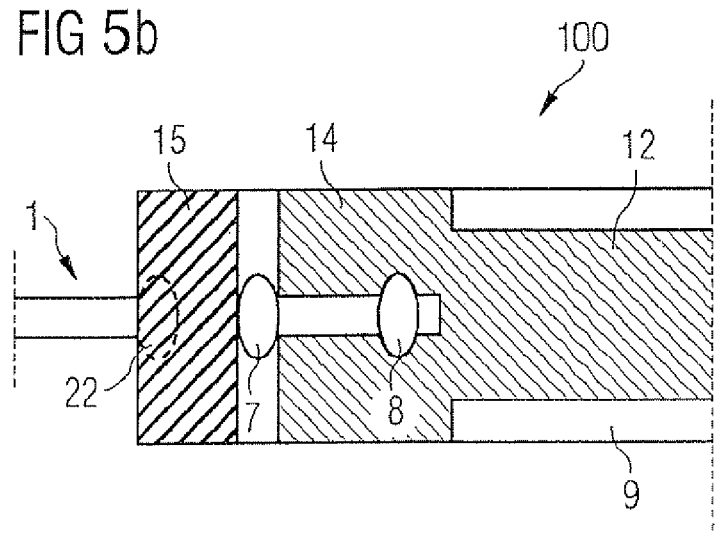

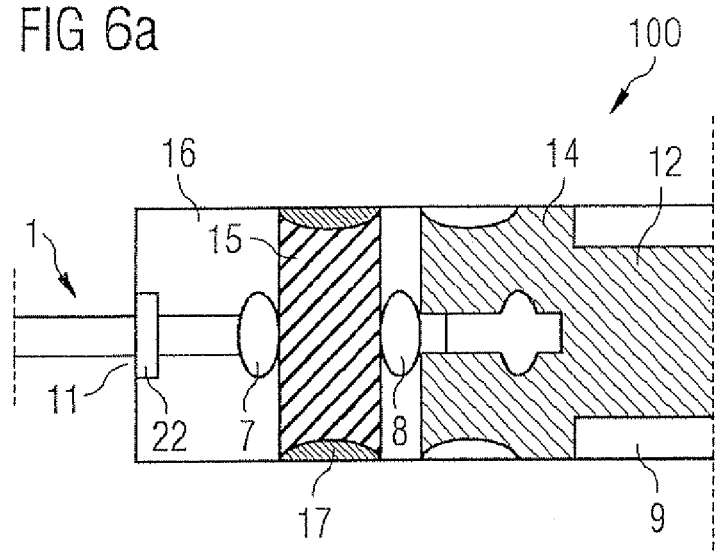
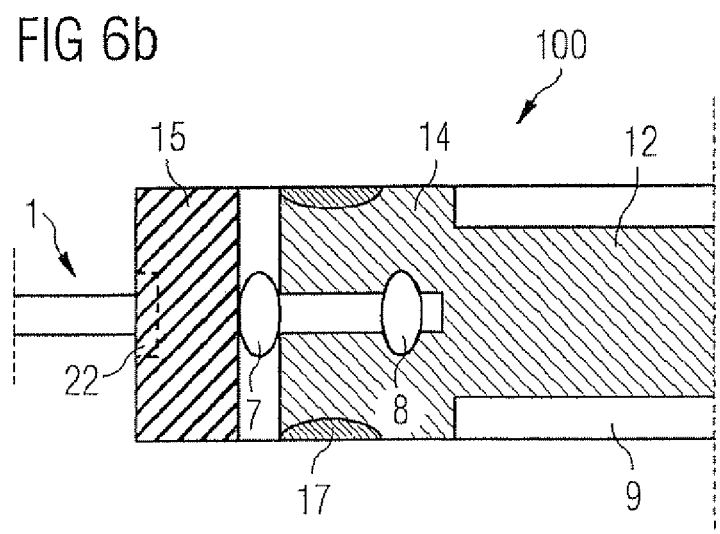

DRUG DELIVERY DEVICE WITH RETRACTABLE NEEDLE

CROSS REFERENCE TO RELATED APPLICATIONS

The present application is a 35 U.S.C. 371 National Application of PCT/EP2010/052786 filed Mar. 4, 2010, which claims priority to European Patent Application No. 09003180.8, filed Mar. 5, 2009, the entire contents of which are incorporated entirely herein by reference.

The invention relates to a drug delivery device comprising a needle.

One problem of existing drug delivery devices, for example of a syringe, especially safety syringes which have retractable needles, is to have a needle which is fixed and does not move with respect to the body of the syringe during the use of the syringe but which can be drawn back into the body of the safety syringe after the use of the syringe. So the needle of the drug delivery device has to be formed in a special way and also has to be arranged in a special way inside the body of the device so that it is fixed during use but movable with respect to the body of the device after use of the drug delivery device.

Most of the common safety syringes with a retractable needle comprise a needle which comprises an arrangement at the inner end which is formed from a material which is different to the needle and which may be formed in complicated geometrical ways to snap mechanically, for example, into other parts of the syringe in a key-lock-mechanism so that the needle arrangement could be later drawn back into the body of the syringe.

One embodiment of the invention is directed to a drug delivery device comprising a needle with a distal end and a proximal end comprises an inner surface forming a channel, an outer surface and a first salient located on the outer surface.

The drug delivery device, which can be a syringe, preferably a safety syringe, comprises a needle, wherein the needle itself has a first salient which is located on the outer surface of the needle. The salient could be, for example, a bulge at the surface, which can have any geometric form, for example hemispherical. Thus it is not necessary to form an additional element around the needle made of another material which can be used to connect the needle with other parts of the syringe, like for example the proximal end of the syringe body or the plunger of the syringe. The connection between the proximal end of the body of the syringe is necessary to locate the needle during the use of the syringe. The connection between the plunger of the syringe and the needle is necessary to draw back the needle into the body unit after the use of the syringe.

In another embodiment, the needle comprises a second salient located on the outer surface between the proximal end and the first salient.

Both of the salients, the first and the second one, can be used on one hand to fix the needle, for example in the body unit of the drug delivery device for the time when the device is used. On the other hand one or both of the salients can be used to connect the needle with another part of the drug delivery device without any additional elements at the outside of the needle, for example coatings or overmoulded features, being necessary.

In another embodiment, the first and second salients comprise the same material as the rest of the needle.

If the two salients are made of the same material as the rest of the needle, the needle and the salients could be formed in the same production step. There are no further production steps necessary to arrange salients at the outside of the needle. This keeps the number of production steps to manufacture the drug delivery device low. Another advantage is that the salients are strongly connected to the needle. The salient may not break away as easily as when the salients are formed around the needle in a separate production step.

The material, the needle and therefore the first and the second salient could be made of, for example, a metal or an alloy.

In another embodiment, the salients are provided by means of an additional element around the needle made of another material. Although this is an additional material and manufacturing step there may be circumstances where this is more straightforward than forming the salients from the needle material. In this embodiment the invention retains the advantage, compared to existing safety syringe devices with retractable needles, that the salients and the needle release mechanism are mechanically simple, comprising only the interaction of a seal and the salient or salients.

In another embodiment, the first salient has a circumferential form surrounding the needle.

This means that the first salient forms a ring around the outer surface of the needle.

In another embodiment, the second salient has a circumferential form surrounding the needle.

This means that the second salient forms a ring around the outer surface of the needle.

In another embodiment, both of the salients, the first and the second, have a circumferential form surrounding the needle.

If the salient has a circumferential form with respect to the needle, the needle could be better fixed inside the body so that it cannot slip out of the fixing in any direction. Also the connection of the needle with other parts of the device is stronger and safer compared to a salient which is located only on one point or one side of the needle.

In another embodiment, the first and the second salients are formed such that their outer diameter continuously increases along the channel up to a maximum and, beyond the maximum, continuously decreases.

If the salients are formed in this way, the needle could be more easily "unlocked" from a fixing, which can be a seal, for example, by pushing the seal over the salient out of its "locking" position into an "unlock" position. If the seal is in the "unlock" position the needle could be moved after the use of the drug delivery device with respect to the body of the device. Also the needle could be more easily connected to another part, the plunger for example, of the drug delivery device.

In another embodiment, the diameter of the channel is constant in the area of the first and the second salient.

The advantage of a constant diameter of the channel over the whole needle is that if, for example, a liquid, is pressed through the needle, the liquid always moves the same distance in the channel for the same volume of liquid which is pressed into the proximal end of the needle. Therefore the liquid could be released by the drug delivery device in constant dosages.

In another embodiment, the drug delivery device additionally comprises a body unit having a first opening and a second opening, a plunger arranged such that its outer end is positioned outside the body unit, and its inner end is positioned within the body unit, wherein the plunger is movable in the distal direction with respect to the body unit, wherein the needle being arranged such that the proximal end and the first and the second salient are positioned within the body unit.

The plunger which is movable with respect to the body unit can be used, on the one hand, to press a liquid which could be, for example, inside the body unit of the drug delivery device through the needle to the distal end of the needle. On the other hand, the plunger could be used after the use of the drug delivery device to get into connection with the needle and to draw back the needle into the body unit after the use of the drug delivery device. The needle with the first and the second salient, which both are positioned inside the body unit, could be fixed during the use of the drug delivery device by means of the first and the second salient and furthermore could be connected over the first and/or the second salient with the plunger to draw back the needle into the body unit after the use of the drug delivery device to avoid the risk of injury, for example, at the distal end of the needle.

In another embodiment, a seal is arranged within the body unit around the needle such that it is located between the first and the second salient.

The seal which is located between the first and the second salient can fix the needle in the body unit, such that the needle does not move with respect to the body unit. The seal itself is fixed between the needle, between the first and the second salient, on one side and the body unit on the other side. Preferably, the seal has a circumferential form with respect to the needle.

In another embodiment the seal comprises a groove at the surface faced to the body unit and the groove has a circumferential form.

The groove can be used to fix the seal in its position, for example by a salient at the inner side of the body unit.

In another embodiment, the seal fixes the needle such that it cannot be moved relative to the body unit.

In another embodiment, a void is located around the needle between the seal and the second opening of the body unit, wherein the void is formed such that it can at least partly house the seal.

The void which is located in the body unit is able to at least partly house the seal, preferably the whole seal. The void has preferably a circumferential form with respect to the needle.

In another embodiment the inner end of the plunger is configured to push the seal to a position where the seal releases the needle.

By means of moving the plunger in the distal direction, the seal can be pushed from the inner end of the plunger such that at least part of the seal or the whole seal is located in the void after being pushed. Thereby, the seal has to move over the first salient, which is a mechanical resistance with respect to the distal movement of the seal. If the seal is located in the void, it is fixed by the first salient so that it cannot move in the proximal direction back into the position between the first and the second salient. When the seal is located in the void it releases the needle.

In another embodiment, the needle is movable in the proximal direction with respect to the body unit when the seal is located on the first salient or between the first salient and the second opening of the body unit.

For example, after pushing the seal with the inner end of the plunger on or over the first salient, the seal is situated on the first salient or between the first salient and the second opening of the body unit. After pushing the seal on or over the first salient, the needle is not fixed as strongly as before and can now be moved in the proximal direction with respect to the body unit. Preferably, the needle cannot move in the distal direction because of the first salient which is now located in or in proximal direction to the seal.

In another embodiment, the inner end of the plunger is configured to be engaged with the first and/or the second salient when the plunger is pushed to a certain position with respect to the needle.

The inner end of the plunger can be configured to be engaged with one of the two salients or with both salients at the same time. When the plunger is pushed in the distal direction, for example to push the seal into the void, the inner end of the plunger can is engaged with one or both salients such that the needle is connected to the plunger. If the plunger is now retracted into the proximal direction, the needle is also retracted into the proximal direction and therefore into the body unit of the drug delivery device.

In another embodiment, the needle is formed such that it can at least be partly retracted into the body unit after being engaged with the plunger.

Formed means, on one hand, that the needle is able to be engaged with the inner end of the plunger and, on the other hand, that it can be moved into the proximal direction, for example, because there is no salient on the distal side of the second opening of the body unit.

In another embodiment, the drug delivery device comprises a boss which is located at the inner surface of the body unit and the boss has a circumferential form surrounding the second opening.

In another embodiment, the seal is moveable onto the boss, where the seal releases the needle.

In another embodiment the drug delivery device comprises a medicament. The medicament could be pre-filled in a cartridge or, if the drug delivery device is designed as a syringe, pre-filled in the syringe.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin;

B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4 (1-39), des Pro36 [Met(O)14 Trp(O2)25, IsoAsp28] Exendin-4 (1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4 (1-39), des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, -continued H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane such as hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The following figures are for illustrating some embodiments of the drug delivery device.

FIG. 1a shows a schematic cross-section of one embodiment of the needle.

FIG. 1b shows a schematic cross-section of another embodiment of the needle wherein the salients have another form.

FIG. 2 shows a schematic cross-section of another embodiment of the needle with second salients.

FIG. 5a/b show a schematic cross-section of a part of an embodiment of the drug delivery device as a section wherein the plunger and the seal are in different positions.

FIG. 6a/b show a schematic cross-section of a part of an embodiment of the drug delivery device wherein the plunger and the seal are in different positions with an additional salient.

Figure 7A:
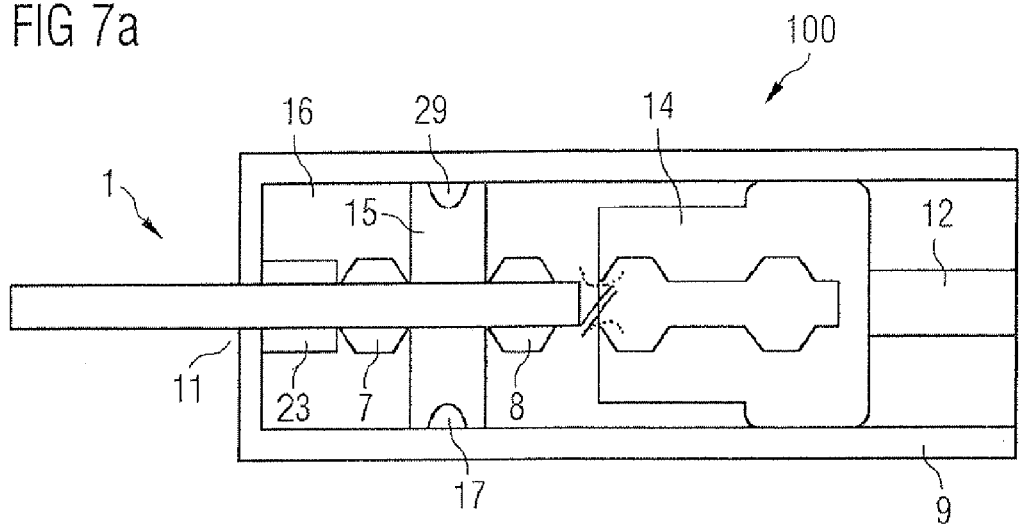

FIG. 7a/b show a schematic cross-section of a part of an embodiment of the drug delivery device as a section wherein the plunger and the seal are in different positions.

FIG. 8a-g show a schematic cross-section of an embodiment of the drug delivery device in seven different steps of use.

FIG. 1a schematically shows the cross-section of one embodiment of the needle 1. The needle 1 comprises a distal end 2, a proximal end 3, an inner surface 4 forming a channel 6, and an outer surface 5. Two first salients 7 are located on the outer surface 5 in opposite positions with respect to the needle 1. The two first salients 7 have a hemispherical form in this embodiment.

FIG. 1b shows a schematic cross-section of another embodiment of the needle 1, which is similar to the embodiment which is shown in FIG. 1a. In this embodiment, which is shown in FIG. 1b, the two first salients 7 have a pyramidal form. Also these two salients are located at the outer surface 5 in opposite positions.

FIG. 2 shows a schematic cross-section of another embodiment of the needle 1. Compared to the needle which is shown in FIG. 1a, the needle in FIG. 2 additionally has two second salients 8. The second salients 8 are located between the first salients 7 and the proximal end 3 of the needle. In this embodiment, the second salients 8 have the same geometric form, which is hemispherical, as the first salients 7. The two second salients 8 are located as the two first salients 7 on opposite sides of the needle 1. In a further embodiment (not shown) the first salients 7 and second salients 8 have a different geometric form.

Figure 3:
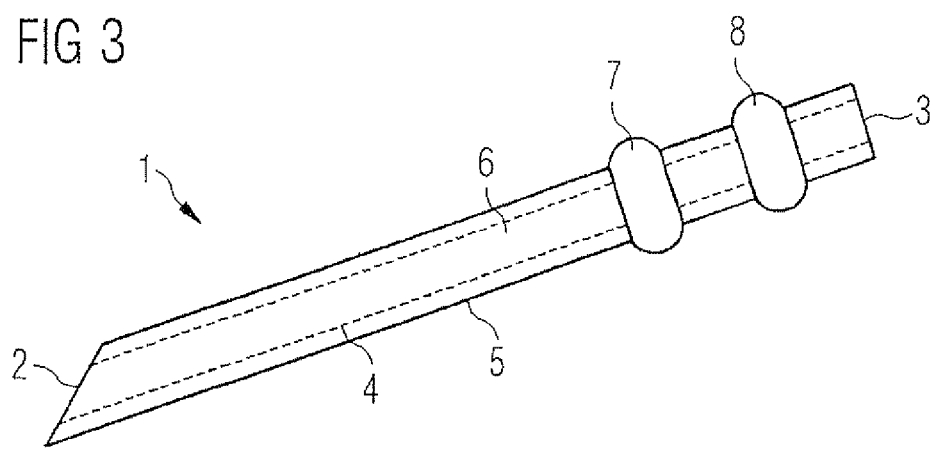
FIG. 3 shows a schematic cross-section of another embodiment of the needle, wherein the first and the second salient have a circumferential form.

FIG. 3 shows a schematic cross-section of another embodiment of needle 1. Compared to the needle which is shown in FIG. 2, the needle which is shown in FIG. 3 has one first salient 7 and one second salient 8. Both of the salients 7,8 have a circumferential form with respect to the needle 1. Circumferential means that both of the salients have a form that they build a ring around the outer surface 5 of the needle 1. In a further embodiment (not shown) the first salients 7 and second salients 8 have a different geometric form, for example second salients 8 may be larger or smaller than first salients 7.

Figure 4:
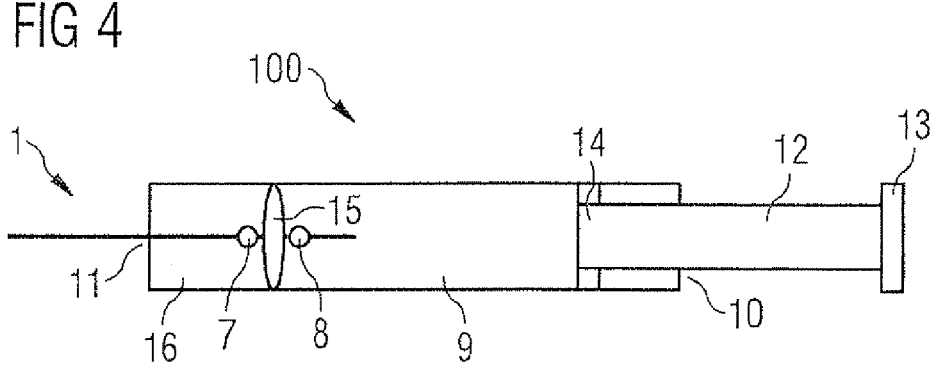
FIG. 4 shows a schematic cross-section of an embodiment of the drug delivery device.

FIG. 4 shows a schematic cross-section of an embodiment of the drug delivery device 100 with its basic elements. This drug delivery device 100 comprises a body unit 9, a needle 1 at the distal end and a plunger 12 at the proximal end. The needle 1 comprises a first and second salient 7,8, which are located inside the body unit 9. A seal 15 is located around the needle 1 and between the first and the second salient 7,8. Inside the body unit 9 there is a void 16 located between the first salient 7 and the second opening 11 of the body unit 9. The void 16 is able to at least partly house the seal 15. The plunger 9 comprises an outer end 13, which is located outside the body unit 9 and an inner end 14, which is located inside the body unit 9. The plunger 12 can be pushed to the distal direction through the first opening 10 with respect to the body unit 9. FIG. 4 only shows schematically how the basic parts of the drug delivery device 100 are arranged relative to each other.

The FIGS. 5a/b each show a schematic cross-section of an section of the drug delivery device 100. In both figures, there is a section of the needle 1 on the left side of the figure and a section of the plunger 12 on the right side of the figure.

In FIG. 5a, the seal 15 is located between the first and the second salient 7,8 and the inner end 14 of the plunger 12 is located on the proximal side of the second salient 8. On the distal side of the first salient 7, there is a void 16 inside the body unit 9. A third salient 22 is located at the second opening 11 of the drug delivery device. This third salient prevents the needle 1 from moving to the distal direction, when it is pushed from the plunger 9 to this direction. There is a void 16 inside the body unit 9 between the first salients 7 and the third salient 22.

The FIG. 5b shows the section of the drug delivery device 100 of the FIG. 5a wherein the plunger 12 with its inner end 14 has been pushed in a distal direction, whereby the seal 15 has been pushed over the first salient 7 into the former void 16. By moving the plunger 12 into the distal direction additionally the inner end 14 of the plunger 12 comes into connection with the needle 1 over the second salient 8 without the needle 1 moving with respect to the body unit 9, because the third salient 22 prevents the needle 1 from moving to the distal direction. The needle 1 may be now not fixed as strongly as before by the seal 15 in its position with respect to the body unit 2. The decrease in connection strength between needle 1 and seal 15 may be caused by a number of means, including, but not limited to, breaking of an adhesive or static frictional bond between the needle 1 and seal 15, the formation of a channel through the central region of seal 15 caused by the travel of the seal 15 over first salient 7 through which the third salient 22 can easily pass, or a difference in size or geometric shape between the first and third salient 7,22, for example third salient 22 is smaller or has an smaller profile compared to first salient 7. Through the connection between the plunger 12 and needle 1 over the inner end 14 of the plunger and the second salient 8 of the needle 1, the needle now can be drawn back into the body unit 9 by means of drawing back the plunger 9 into proximal direction.

The FIGS. 6a/b show a similar embodiment to that which is shown in the FIGS. 5a/b. The embodiment shown in FIGS. 6a/b additionally has a salient 17 located at the inner side of the body unit 9. The salient 17 located at the inner side of the body unit is running circumferentially around the whole inner side of the body unit 9. The salient 17 is located between the first and the second salient 7,8 at the initial position of the seal 15 as shown in FIG. 6a. The salient at the inner side of the body unit 9 additionally fixes the seal 15 in its position The third salient 22, which is located at the second opening 11, has the form of a disc in this embodiment, which runs circumferentially with respect to the needle 1. The third salient 22 prevents the needle 1 from moving into the distal direction with respect to the body unit 9, when a pressure impacts onto the needle 1 or the seal 15 from the proximal direction. Through the pressure from outside of the seal 15, the needle 1 is fixed more strongly, in both proximal and distal directions, in this position, for example by salient 17 providing increased compression of the seal 15 which in turn creates additional mechanical resistance to axial displacement of the seal 15 and therefore needle 1.

When the seal 15 is pushed into the former void 16 as shown in FIG. 6b, the compressive force on the seal 15 is reduced because the salient 17 no longer provides additional compression to the seal 15. Therefore the needle 1 which runs through the seal 15 is not fixed as strongly as before when the seal 15 was located between the two salients 7,8. The salient 17 of the inner side of the body unit 9 is fixedly connected with the body unit 9 and does not move with the seal 15 into the former void 16. When the plunger 12 is moved into the distal direction and pushes the seal 15 into the former void 16, now the inner end of the plunger 14 moves to the former position of the seal 15. Therefore, the distal end of the inner end 14 of the plunger 9 is now in the position the seal 15 has been before. The parts of the inner end 14 of the plunger which have been pushed apart to overcome the second salient 8 are now being pushed together in the outgoing position by the salient 17 which is located in the inner side of the body unit 9. The compression from the outside onto the inner end 14 of the plunger strengthens the connection between the needle 1 and the plunger 12. Therefore, the needle 1 is now fixedly connected to the plunger 12 and could be drawn back by means of moving the plunger 12 into the proximal direction with respect to the body unit 9 such that the whole needle 1 is in the end located inside the body unit 9.

The FIGS. 7a/b show a similar embodiment to that which is shown in the FIGS. 6a/b. The embodiment shown in FIGS. 7a/b has an additional boss 23, through which needle 1 passes, and does not have a third salient on the needle.

The embodiment shown in FIGS. 7a/b has a salient 17 located at the inner side of the body unit 9. The salient 17 located at the inner side of the body unit runs circumferentially around the whole inner side of the body unit 9. The salient 17 is located between the first and the second salient 7,8 at the initial position of the seal 15 as shown in FIG. 7a. The salient 17 at the inner side of the body unit 9 additionally fixes the seal 15 in its position thus that the seal 15 is arranged in a way, that its groove 29 is located at the salient 17, for example by providing increased compression of the seal 15 which in turn creates additional mechanical resistance to axial displacement of the seal 15. The boss 23, which is located at the second opening 11, is in contact with the first salient 7. The hole in the boss 23, through which the needle passes, is a smaller diameter than the diameter of the first salient 7. Therefore needle 1 is prevented from moving in the distal direction with respect to the body unit 9, when a pressure impacts onto the needle 1 or the seal 15 from the proximal direction. In this position friction between the needle 1 and the seal 15 and the interaction of the first salient 7 and seal 15 prevents the needle 1 from moving in the proximal direction. In this position salient 17 provides increased compression of the seal 15 which in turn creates additional mechanical resistance to axial displacement of the seal 15 and therefore needle 1.

Figure 7B:
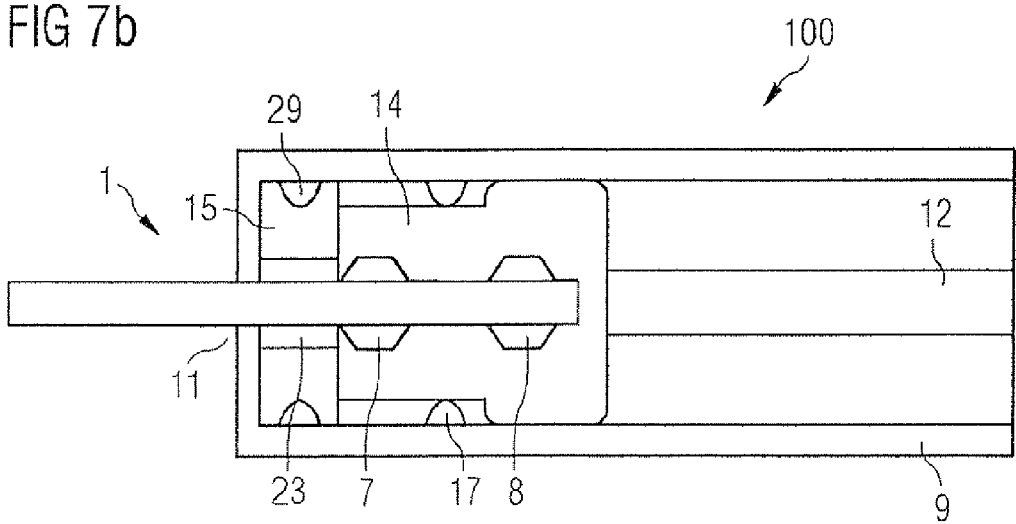

When the seal 15 is pushed into the former void 16 as shown in FIG. 7b, the compressive force on the seal 15 is reduced because the salient 17 no longer provides additional compression to the seal 15. Seal 15 is pushed over the first salient 7 and onto the body protrusion 23. In this position the needle 1 is no longer in contact with seal 15. The salient 17 of the inner side of the body unit 9 is fixedly connected with the body unit 9 and does not move with the seal 15 into the former void 16. When the plunger 12 is moved into the distal direction and pushes the seal 15 into the former void 16, the inner end of the plunger 14 occupies the former position of the seal 15. The distal end of the inner end 14 of the plunger 9 is now pushed into position over first and second salients 7,8. Therefore, the needle 1 is now fixedly connected to the plunger 12. The hole in boss 23 through which needle 1 passes is larger than the needle outer diameter and therefore provide no resistance to proximal movement of the needle 1. The needle 1 could be drawn back by means of moving the plunger 12 into the proximal direction with respect to the body unit 9 such that the whole needle 1 is in the end located inside the body unit 9.

The FIGS. 8a to 8g show a schematic cross-section of an embodiment of a drug delivery device 100 in seven different steps of use.

Figure 8A:
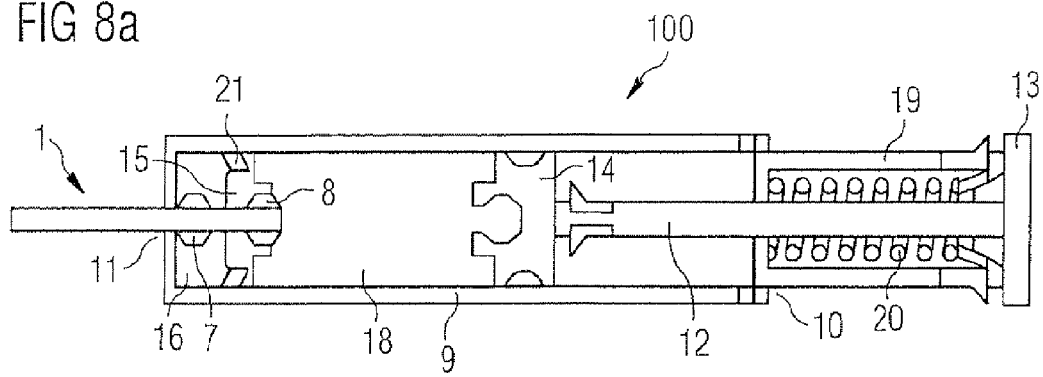

FIG. 8a shows an embodiment of the drug delivery device 100 in a schematic cross-section. The drug delivery device 100 comprises a needle 1 with a first salient 7 and a second salient 8. The needle 1 is located with respect to the body unit 9 in a way that the first salient 7 and the second salient 8 are located inside the body unit 9. The drug delivery device 100 further comprises a plunger 12 with an outer end 13 and an inner end 14. The proximal part of the plunger 12 is surrounded by a sleeve 19. Inside the sleeve 19 round the plunger 12 a spring 20 is arranged. The spring 20 is pre-compressed into a stressed condition. The body unit 9 comprises a first opening 10 at its proximal end and a second opening 11 at its distal end. Between the first salient 7 and the second salient 8 there is a seal 15 which is formed circumferentially with respect to the needle 1 and which is with its outer end and in contact to a protrusion 21 which is located at the inner side of the body unit 9. The chamber between the inner end 14 of the plunger 12 and the seal 15 is filled with a liquid 18, which could be a drug for example. The seal 15 prevents the liquid 18 from running into the void 16. FIG. 8a shows the drug delivery device 100 in its starting position.

Figure 8B:
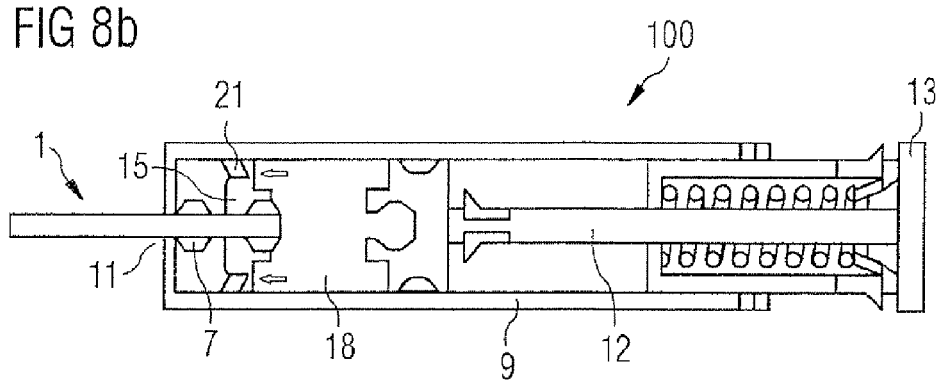

FIG. 8b shows an intermediate step of the use of the drug delivery device 100 which is shown in FIG. 8a. By pushing on the outer end 13 of the plunger 12 the plunger 12 moves with respect to the body unit 9 to the distal direction. By moving the plunger 12 in the distal direction the liquid 18 which is inside the body unit 9 is pressed through the needle 1 and onto the proximal side of the seal 15. The flange of the seal 15 is pressed onto the protrusion 21. So the seal is fixed with respect to the body unit 9 and therefore the needle 1 is fixed also with respect to the body unit 9 by the seal 15. The flange of the seal 15 has a relatively large surface area because it is at the outside diameter of the body unit 9. The liquid 18 pressure against the flange and angled protrusions 21 creates frictional forces between flange and protrusions 21 preventing the seal 15 being pushed in the distal direction. Furthermore, the needle 1 cannot move into the distal direction with respect to the body unit 9 because of the first salient 7 which is located inside the second opening 11 of the body unit 9.

Figure 8C:
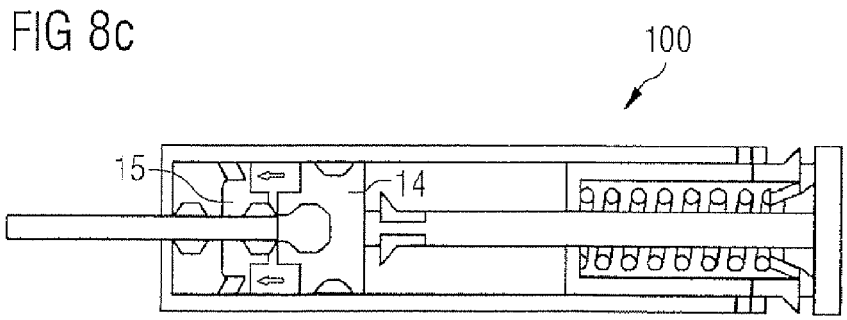

FIG. 8c shows a further intermediate step of the use of the drug delivery device 100 which is shown in FIG. 8a. Through moving the inner end 14 of the plunger into the distal direction, now the inner end 14 has a direct contact to the seal 15. The distal end of the inner end 14 of the plunger can now apply a force directly to the proximal end of the seal 15.

Figure 8D:
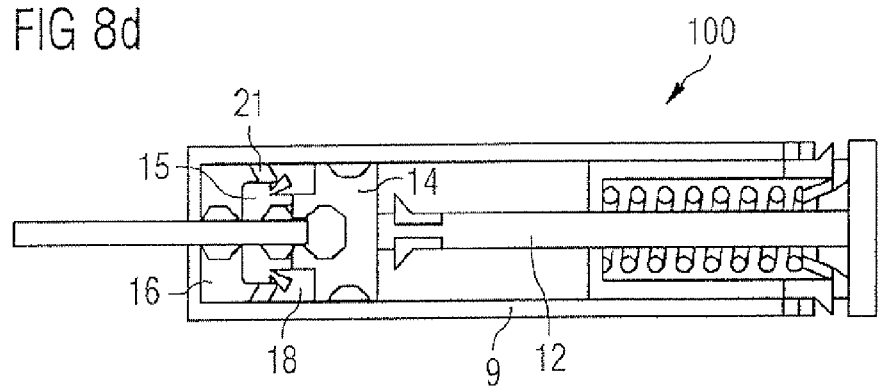

FIG. 8d shows a further intermediate step of the use of the drug delivery device 100 which is shown in FIG. 8a. By further pushing the plunger 12 into the distal direction with respect to the body unit 9 the inner end 14 which was in direct contact before with the seal 15 now pushes the seal 15 in the distal direction with respect to the needle 1 in a way that the seal 15 loses the direct contact to the protrusion 21. The flange of the seal 15 is pulled away from protrusions 21. During this the needle 1 stays in its position with respect to the body unit 9. The seal 15 still prevents the fluid 18 from running into the void 16.

Figure 8E:
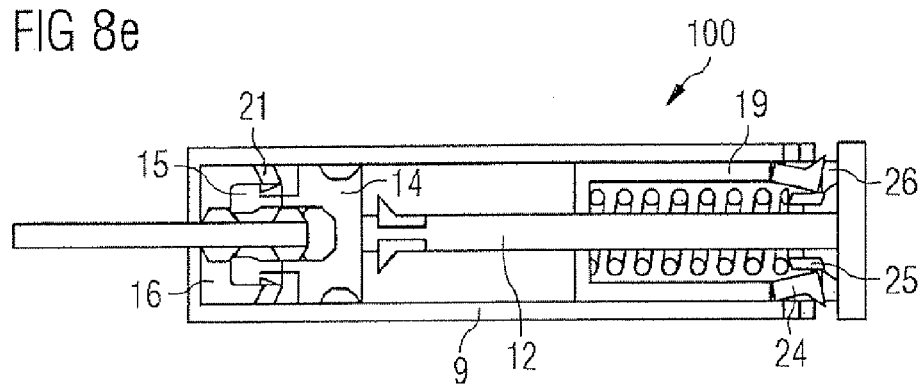

FIG. 8e shows another intermediate step of the use of the drug delivery device 100 which is shown in FIG. 8a. After the seal 15 has lost the contact to the protrusion 21 it can be pushed in the distal direction into the void 16 by pushing the plunger 12 with its inner end 14 into the distal direction. The snap arms 24 of the sleeve 19 are forced inwards by contact with the body unit 9. In turn the sleeve snap arms 24 cause the plunger rod latch arms 25 to deform inwards. The plunger rod latch arms 25 snap inwards over sleeve latch features 26. The spring 20 now exerts a force in the proximal direction on the plunger 12. Proximal movement of the plunger 12 is resisted by pressure applied manually to the proximal end surface of plunger 12.

Figure 8F:
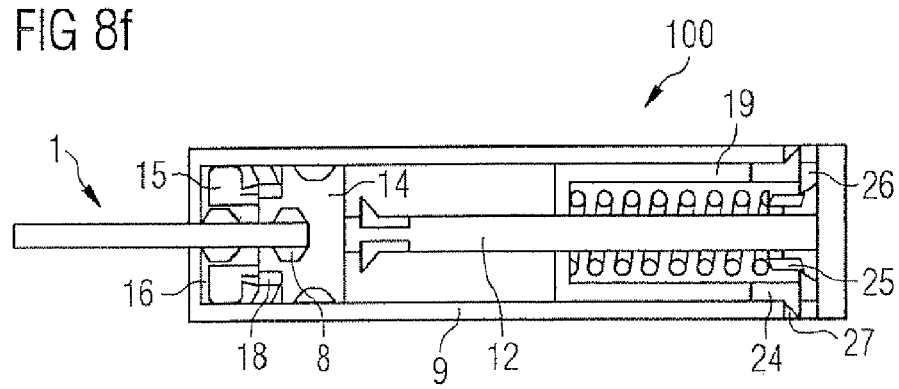

FIG. 8f shows another intermediate step of the use of the drug delivery device 100 which is shown in FIG. 8a. In this step now the seal 15 is located in the void 16. Therefore the seal 15 no longer offers a resistance to the needle 1 to be retracted. The inner end 14 of plunger 12 has now snapped over the second salient 8. Hereby the needle 1 is now connected to the plunger 12 over the second salient 8. The seal 15 still prevents the fluid 18 from running into the void 16 by sealing the areas in which the rest of the fluid 18 is located against the void 16. Only a very small and controlled amount of the liquid 18 stays in the drug delivery device 100. The sleeve snap arms 24 lock into recesses 27 of the body unit 9. Therefore the sleeve 19 is now connected to the body unit 9 and can no longer move with respect to the body unit 9. The plunger rod latch arms 25 of the plunger 9 remain in their deformed condition clear of the sleeve latch features 26.

Figure 8G:
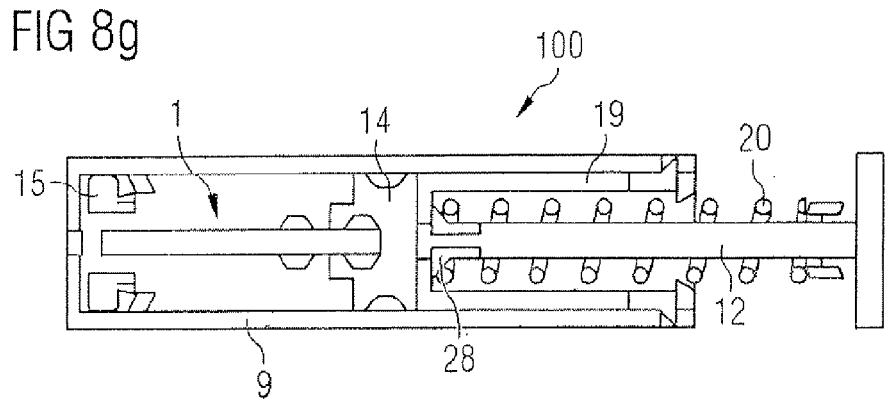

FIG. 8g shows another intermediate step of the use of the drug delivery device 100 which is shown in FIG. 8a. After connecting the plunger 12 over its inner end 14 with the needle 1 and after separating the seal 15 from the needle 1, the needle 1 can now be drawn back with respect to the body unit 9 in the proximal direction by the spring 20, which was pre-stressed. The needle 1 can be drawn back so far that the whole needle 1 is located inside the body unit 9. In the end position the inner end 14 contacts the sleeve 19. The plunger rod snap arms 28 deflect inwards as they pass through a hole in the distal end surface of sleeve 19. Once the plunger rod snap arms 28 are clear of the hole in sleeve 19 the plunger rod snap arms 28 flex outwards to lock the plunger 12 in the rearward position relative to the sleeve 19 and prevents the needle 1 from moving in the distal direction.

REFERENCE NUMERALS 1) needle
2) distal end
3) proximal end
4) inner surface
5) outer surface
6) channel
7) first salient
8) second salient
9) body unit
10) first opening
11) second opening
12) plunger
13) outer end
14) inner end
15) seal
16) void
17) salient at the inner side of the body unit
18) liquid
19) sleeve
20) spring
21) protrusion
22) third salient
23) boss
24) snap arms
25) plunger rod latch arms
26) sleeve latch features
27) recesses
28) plunger rod snap arms
29) groove
100) drug delivery device

The invention claimed is:

1. Drug delivery device, comprising:
a needle with a distal end and a proximal end, which comprises:
an inner surface forming a channel,
an outer surface,
a first salient located on the outer surface,
a second salient located on the outer surface between the proximal end and the first salient,
a body unit having a first opening and a second opening,
a plunger arranged such that an outer end of the plunger is positioned outside the body unit, and an inner end of the plunger is positioned within the body unit, wherein the plunger is moveable in the distal direction with respect to the body unit, and wherein the needle is arranged such that the proximal end and the first and second salient are positioned within the body unit, and
a seal arranged within the body unit, wherein the seal contacts the outer surface of the needle such that the seal is interposed between the first and second salient thereby separating the first salient from the second salient by a distance, wherein in a first position the seal fixes the needle such that it cannot be moved relative to the body unit, wherein the inner end of the plunger is configured to push the seal to a second position where the seal releases the needle, and wherein the inner end of the plunger is configured to be engaged with the first and/or the second salient when the seal is pushed to a second position.

2. Drug delivery device according to claim 1, wherein the first and second salients comprise the same material as the rest of the needle.

3. Drug delivery device according to claim 1, wherein the first salient has a circumferential form surrounding the needle.

4. Drug delivery device according to claim 1, wherein the second salient has a circumferential form surrounding the needle.

5. Drug delivery device according to claim 1, wherein the first and the second salients are formed such that their outer diameters continuously increase along the channel up to a maximum and, beyond the maximum, continuously decrease.

6. Drug delivery device according to claim 1, wherein the seal comprises a groove at an inner surface of the body unit and the groove has a circumferential form.

7. Drug delivery device according to claim 1, wherein the body unit comprises:
a void located around the needle between the seal and the second opening of the body unit, wherein the void is formed such that it can at least partly house the seal.

8. Drug delivery device according to claim 1, wherein the needle is moveable in a proximal direction with respect to the body unit when the seal is located between the first salient and the second opening of the body unit.

9. Drug delivery device according to claim 1, wherein the needle is formed such that it can at least be partly retracted into the body unit after being engaged with the plunger.

10. Drug delivery device according to claim 1, wherein the drug delivery device comprises a boss which is located at an inner surface of the body unit and the boss has a circumferential form surrounding the second opening.

11. Drug delivery device according to claim 10, wherein the seal is moveable onto the boss, where the seal releases the needle.

12. Drug delivery device according to claim 1, comprising a medicament.

* * * * *

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

```
Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
            35
```